United States Patent [19]

Osaki et al.

[11] Patent Number: 4,710,700
[45] Date of Patent: Dec. 1, 1987

[54] METHOD OF MEASURING ORIENTATION OR DIELECTRIC CHARACTERISTIC OF DIELECTRIC SHEETS OR WEBS

[75] Inventors: Shigeyoshi Osaki, Hyogo; Yoshihiko Fujii, Osaka, both of Japan

[73] Assignee: Kanzaki Paper Manufacturing Co., Ltd., Tokyo, Japan

[21] Appl. No.: 777,453

[22] Filed: Sep. 18, 1985

[30] Foreign Application Priority Data

Sep. 22, 1984 [JP] Japan .................................. 59-199225

[51] Int. Cl.[4] ........................ G01R 27/04; G01B 5/16
[52] U.S. Cl. .................................. 324/58.5 A; 73/159; 324/58.5 R
[58] Field of Search .................... 73/159; 324/58.5 A, 324/58.5 B, 58.5 C, 58.5 R

[56] References Cited

U.S. PATENT DOCUMENTS 4,087,746 5/1978 Kanae .............................. 324/58.5 A
4,297,874 11/1981 Sasaki ............................. 324/58.5 C
4,581,575 4/1986 Osaki .............................. 324/58.5 C

FOREIGN PATENT DOCUMENTS 0039447 4/1981 Japan .............................. 324/58.5 C

OTHER PUBLICATIONS

Tiuri: "Microwave Method for Measurement of Fiber Orientation . . . ", 4th European Microwave Conference-pp. 137-140.
Tappi Standard T481 SM-60, Suggested Method–1952, Revised–1960, "Fiber Orientation and Squareness of Paper".

Primary Examiner—Reinhard J. Eisenzopf
Assistant Examiner—Jose M. Solis
Attorney, Agent, or Firm—Morgan & Finnegan

[57] ABSTRACT

A method of measuring the orientation or dielectric characteristic of a dielectric sheet or web is disclosed, with the steps of inserting a sample portion of the dielectric sheet or web in a small clearance in a cavity resonator formed of a pair of waveguides respectively having a transmitting antenna and a receiving antenna, said waveguides being spaced apart from each other with their openings defining said clearance therebetween, irradiating said sample portion with frequency sweep type linearly polarized microwaves from the upper waveguide perpendicularly to said sample portion while producing a relative rotational motion between the plane of polarization of microwaves and said sample portion around the axis of said cavity resonator, and measuring the resonance frequency or Q value of the microwaves received by the lower waveguide.

2 Claims, 11 Drawing Figures

Longitudinal axis

Fig. 6.

Longitudinal axis

Fig. 7.

Longitudinal axis

Longitudinal axis

Fig. 11.

Longitudinal axis

METHOD OF MEASURING ORIENTATION OR DIELECTRIC CHARACTERISTIC OF DIELECTRIC SHEETS OR WEBS

TECHNICAL FIELD

The present invention relates to a method of measuring the molecular orientation or dielectric characteristic of a dielectric sheet or web in a very simple manner and in a short time.

PRIOR ART

To obtain a dielectric sheet or web (hereinafter referred to briefly as "sheet") of high quality it is important, where the dielectric sheet is a paper sheet, to disperse fibers sufficiently to obtain as low a concentration as possible and then screen them uniformly for paper making. However, the viscosity force of paper stock developed when the stock is spouted at high speed from the head box or the dragging force exerted on the paper stock by the wire cloth, on which it is carried, traveling at a speed almost equal to the flow rate of stock causes the fibers to be oriented in the direction of flow, thus producing differences in paper strength and gloss between longitudinal and transverse directions. Particularly, if during operation operator makes a mistake in setting the slice flow collision position, the positional relation between the breast roll, wire cloth and forming board or other operating conditions, abnormally variant orientations of fibers take place, imparting a great deal of anisotropy to the paper, which, in turn, forms a cause of frequent paper break at the wet end or marked ununiformity of coating color profile when a coating color is applied to the paper by a coater.

Further, in the phase of final product, since dimensional changes due to variations in the humidity of the atmosphere are irregular, curls and wrinkles are formed.

Conventionally, to detect such abnormality of fiber orientation in its early stage, a sample of paper is taken at the reel part of the paper making machine as soon as the paper roll is wound up and the sample is tested as by measurement of zero-span tensile strength method (TAPPI, STD, T481 sm-60), ultra-sonic method, X-ray diffraction method, or viscoelasticity spectroanalysis.

PROBLEMS TO BE SOLVED BY THE INVENTION

Such methods, however, involve a troublesome procedure for setting a sample strip such as a sheet or a sample protion in the measuring mechanism and takes a long time in ascertaining the abnormality of fiber orientation. Thus, if there is an abnormality, a large amount of reject would be produced before the completion of a checkup of fiber orientation over the entire width of the machine, paticularly a modern machine which has been sped up and increased in width.

In the case of forming a dielectric sheet of plastic material, a non-stretched sheet is produced either by the tubular film process in which the sheet material is first heated or friction-melted to be given fluidity and then extruded into a cylindrical form, into which air is blown to inflate it and at the same time it is externally cooled for solidification or by the T-die process in which the melt is extruded into a smooth thin film form and then cooled for solidification in a water tank or on a cooling drum. However, such non-stretched sheet is too inferior in such mechanical strengths as tensile strength, impact strength and tear strength and in processability to be used as such. Thus, to obtain a sheet of good quality, the non-stretched sheet is heated to a suitable temperature above its softening point but below its melting point and subjected to uniaxial or biaxial stretching to improve its physical properties. In such stretching process, it does not necessarily follow that simply mechanically stretching the non-stretched sheet provides a sheet of good quality, but it is necessary that the stretching be performed to provide a particular orientation of molecules to agree with the intended use of the sheet product.

In the case of forming a dielectric sheet of ceramic material, a fine ceramic powder is mixed with a binding agent and a lubricant to produce a slip, which is then poured onto a continuously traveling tape of polyethylene or Teflon, and after the thickness of the slip layer on the tape is adjusted as by a doctor, it is fired and finished, the process being called the tape casting forming method, whereby a ceramic sheet in thin film form is obtained.

Such thin film-like ceramic sheets are used as a material for laminated ceramic capacitors, for example, by laminating them alternately with electrodes. For the application of ceramic sheets to such use, it is of utmost importance from the standpoint of securing the quality of capacitors at high level that the dielectric constant across the width of ceramic sheets be substantially uniform. Therefore, a checkup of widthwise molecular orientation corresponding to dielectric constant must be made so that only those ceramic sheets which are appropriate may be used. Therefore, said plastic films and ceramic films must be tested for their molecular orientation as in the case of fiber sheets. Thus, conventionally, in these sheets, as soon as the roll is wound up at the winder part of said stretching machine or tape casting forming device, a sample is taken and tested for the presence or absence of abnormality of molecular orientation as by elastic modulus measurement, X-ray diffraction method, or infrared absorption spectroanalysis. With these methods, however, there is the same drawback as was previously described in connection with paper sheets, that is, a large amount of reject would be produced before the completion of the checkup of molecular orientation of the sheet product across the entire width of the processing machine.

As for dielectric characteristic which is one of the electrical characteristics of dielectric sheets such as those described above, as a result of the increasing use of high frequency waves in the electrical communications field it has become very important, in selecting IC boards or dielectric materials for high frequency cables, to know their dielectric characteristics. Therefore, in the industry there has been a demand for establishing a measuring method which is simple and yet relatively accurate. However, the fact is that even in a high frequency dielectric characteristic measuring method using a reentrant cylindrical cavity resonator, which is said to be a relatively simple method, a measurement can only be made by separating the intermediate portion of the central conductor of the cavity resonator to form a parallel capacitor and putting a specimen therein; thus, much time is involved in putting a specimen in and out, so that it is impossible to make a large number of measurements in a short time.

SUMMARY OF THE INVENTION

An object of the invention is to provide a method of measuring the molecular orientation or dielectric characteristic of a dielectric sheet in a very simple manner and in a short time.

More particularly, the invention provides a method of measuring the orientation or dielectric characteristic of a dielectric sheet or web, characterized by inserting a sample portion of the dielectric sheet or web in a small clearance in a cavity resonator formed of a pair of waveguides respectively having a transmitting antenna and a receiving antenna, said waveguides being spaced apart from each other with their openings defining said clearance therebetween, irradiating said sample portion with frequency sweep type linearly polarized microwaves from the upper waveguide perpendicularly to said sample portion while producing a relative motion between the plane of polarization of microwaves and said sample portion around the axis of said cavity resonator, and measuring the resonance frequencey or Q value of the microwaves received by the lower waveguide.

In order to ascertain the orientation state of the molecules of a dielectric sheet, we have investigated the use of and experimented with a microwave having the nature of being considerably attenuated by the molecules presence and we have found that if frequency sweep type linearly polarized microwaves (hereinafter referred to briefly as linearly polarized waves) are applied, at right angles, to said sheet while rotating the latter in a plane, and if the sheet has molecular orientability, the resonance frequency value varies and that the angle at which the deviation of resonance frequency is related to the direction of orientation of the molecules.

We have also found that since the Q value also varies with said deviation of resonance frequency value, the dielectric constant and dielectric loss correspondingly vary.

Such fact can also be verified by the following equations we have derived. Where the inductance of the cavity resonator system including a sheet is represented by $L$ ($\Omega$), the capacitance by $C$ (F), and the resonance frequency by $f$ (Hz), equation (1) is obtained.

$$f = \frac{1}{2\pi \sqrt{LC}} \tag{1}$$

Let $C_1$ be the capacitance of the resonator system and $C_2$ be the capacitance of the sheet, then $C$ is expressed by equation (2).

$$\frac{1}{C} = \frac{1}{C_1} + \frac{1}{C_2} \tag{2}$$

Let $\epsilon_o$ be the dielectric constant of the cavity resonator system where there is no sheet, $\epsilon_2$ be the dielectric constant of a sheet, $d_1$ and $s$ be the clearance and area of the openings in the waveguides, respectively, and $d_2$ be the thickness of the sheet, then $C_1$ and $C_2$ in equation (2) are expressed by equations (3) and (4)

$$C_1 = \epsilon_0 \frac{S}{d_1 - d_2} \tag{3}$$

$$C_2 = \epsilon_2 \epsilon_0 \frac{S}{d_2} \tag{4}$$

Let $f_o$ be the resonance frequency where there is no sheet, then from equations (1), (2) and (3) the resonance frequency $f$ is given by the following equation.

$$f = f_0 \left\{ 1 - \frac{d_2}{d_1} \left( \frac{\epsilon_2 - 1}{\epsilon_2} \right) \right\}^{\frac{1}{2}} \tag{5}$$

In addition, with the dielectric dispersion assuumed to be associated with Debye relaxation, the dielectric constant is given by equation (6).

$$\epsilon_2 = C_3 \frac{N\mu^2 \cos^2(\theta - \phi)}{\Gamma} + C_4 \tag{6}$$

where $\Gamma$ is a function of the recovery force in and between molecules with respect to torsion, $N$ is the number of dipoles per unit volume, $\mu$ is the effective dipole moment, and $C_3$ and $C_4$ are constants.

From equations (5) and (6), $f$ is given by the following equation.

$$f = f_0 \left\{ 1 - \frac{d_2}{d_1} \left( \frac{C_3 N\mu^2 \cos^2(\theta - \phi) + C_4 - 1}{C_3 N\mu^2 \cos^2(\theta - \phi) + C_4} \right) \right\}^{\frac{1}{2}} \tag{7}$$

It is seen from equation (7) that when the direction of change in the orientation of the dipoles of the molecules of the sheet coincides with the direction of the polarization plane of microwaves, the deviation of the resonance frequency is at a maximum.

Complex dielectric constant $\epsilon^*$ is related to dielectric constant $\epsilon_2$ and dielectric loss $\epsilon_2''$ by equation (8).

$$\epsilon^* = \epsilon_2 - j\epsilon_2'' \tag{8}$$

Let $l$ be the length of a rectangular waveguide, $Q$ be the Q value of the cavity resonator where there is a sheet, and $Q_o$ be the Q value of the cavity resonator system where there is no sheet, then $\epsilon_2$ and $\epsilon_2''$ in equation (8) can be approximated as indicated by equations (9) and (10).

$$\epsilon_2 = 1 + \frac{l(f_0 - f)}{d_2 f} \tag{9}$$

$$\epsilon_2'' = \frac{l}{2d_2} \left( \frac{1}{Q} - \frac{1}{Q_0} \right) \tag{10}$$

If, therefore, $f_o$ and $Q_o$ are found beforehand and values of $f$ and $Q$ for each angle are measured, then $\epsilon_2$ and $\epsilon_2''$ can be found by computation.

PREFERRED EMBODIMENTS

Figure 1:
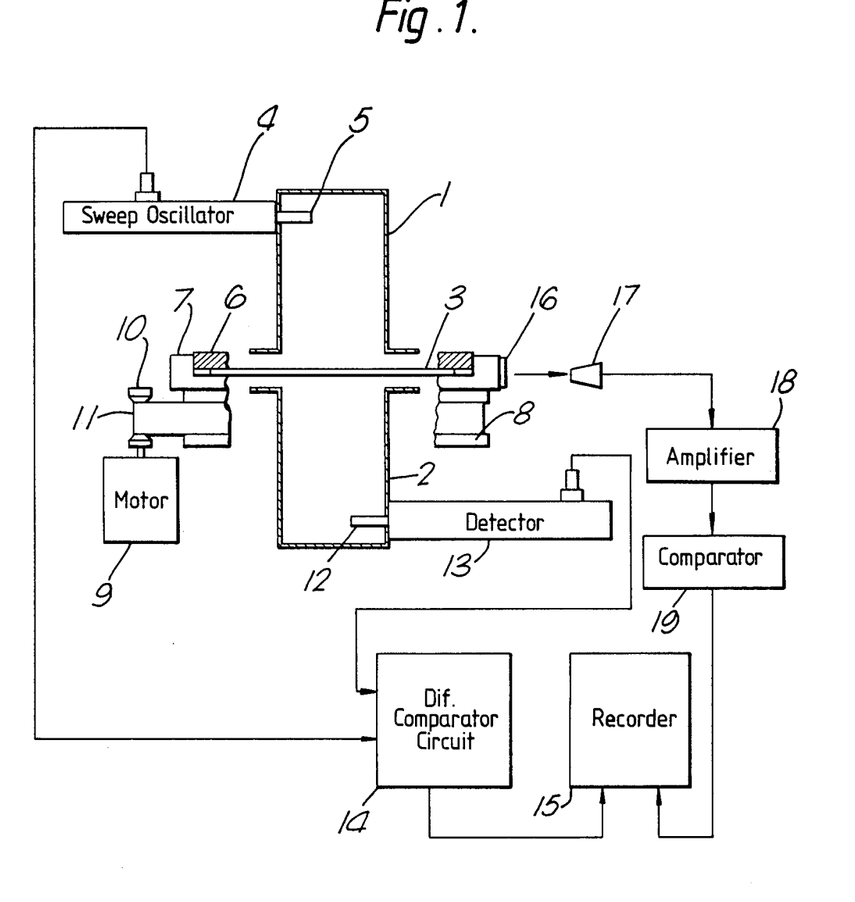
FIGS. 1, 3 and 4 are schematic views showing an embodiment of a molecular orientation or dielectric characteristic measuring apparatus used in the present invention.

The method of the invention will now be described in more detail with reference to the drawings. FIG. 1 schematically shows an embodiment of an apparatus used for the method of measuring the molecular orientation and dielectric characteristic of a sheet according to the invention. The numeral 4 denotes a sweep oscillator which emits linearly polarized sawtooth waves (5 Hz sweep) in the range of 4.9–5.0 GHz, for example. The microwaves are emitted from a transmitting antenna 5 so that they fall on the surface of a sheet 3 always at right angles thereto. In addition, microwaves which are usable are in the range of hundreds of MHz to 100 GHz, but since attenuation due to rearrangement of the molecules of sheets takes place more readily at frequencies of less than 1 GHz, it is more preferable to use microwaves of about 1–30 GHz. As for sheets that can be measured, mention may be made of fiber sheets such as paper sheets, plastic sheets such as are made of polyethylene, polyoxymethylene, polyvinyl chloride, polyvinylidene fluoride, polyethylene terephthalate, polyamides, polyimides or copolymers of their and other polymers, ceramic sheets such as are made of alumina, alumina silicate, barium titanate, titanium oxide, silicon carbide, strontium titanate, carbon sheets, carbon fiber-containing plastic sheets living membrane sheets, ionic equilibrium membrane sheets, and cellular sheets encapsulating a material such as high molecular liquid crystal, polymer solvent, colloidal solvent, gel materials, or short filament dispersing fluid. In addition, since dielectric sheets tend to exhibit higher dielectric constants when molecules have polarity, the deviation of microwave frequency can be measured more efficiently for orientable sheets having polar groups in their molecules. As for samples, those in the form of circles of quandrangles larger than the flange of an upper waveguide 1 are used. To retain such sheet 3 in a clearance defined between the upper waveguide 1 and a lower waveguide 2, a sheet fixing block 7 or the like having a keep ring 6 in the upper groove section is installed.

To rotate the sheet fixing block 7 with the sheet fixed thereon at a fixed speed, there is employed a method in which for example as shown in FIG. 1, a drive belt 11 is entrained in a belt drive groove 8 formed in the lateral lower portion of the sheet fixing block 7 and in a groove in a drive pulley 10 on the front end of a variable speed motor 9 and the latter is driven. In addition, a stepping motor may be used as said variable speed motor. The linearly polarized microwaves attenuated by the molecules in the sheet 3 are received by a receiving antenna 12 after they have passed through the lower waveguide 2, and they are converted into electric signals. Such electric signals are demodulated by a detector 13 and then fed to a differentiating and comparing circuit 14. Since the resonance frequency in this case is the frequency at which the detected output obtained during sweep is at a maximum, the frequency for which the differentiated value from the differentiating and comparing circuit 14 is zero is taken as the resonance frequency. The resonance frequency obtained is recorded by a recorder 15.

Figure 2:
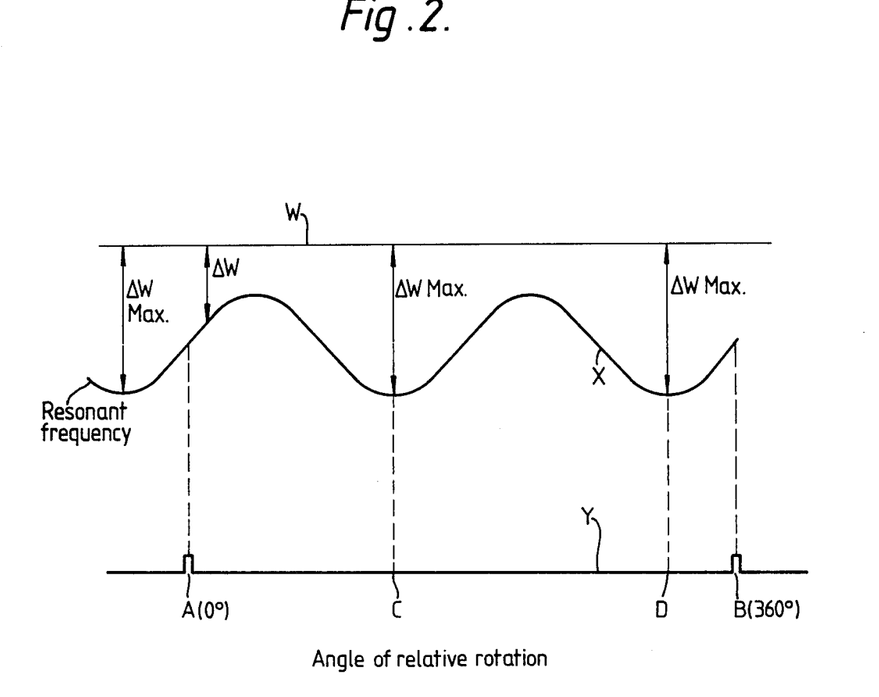
FIG. 2 is a diagram for explaining the determination of molecular orientation by using graphs recorded on a chart in a recording section.

The resonance frequency curve recorded on the chart in the recorder is as shown in FIG. 2. To provide a rotative angle reference for this resonance frequency curve X, for example as shown in FIG. 1, a narrow reflecting tape 16 is applied to only one place on the lateral surface of the sheet fixing block 7 so that variations in reflectance of monitor light are detected during rotation by an optical sensor 17 and the resulting electric signals are transferred via an amplifier 18 and a comparator 19 to the recorder 15, whereby they are recorded on the chart as shown at Y in FIG. 2. In addition, since the transverse or longitudinal direction of the sheet is known in advance, the sheet 3, when attached to the sheet fixing block 7, is positioned so that for example the upstream side of the longitudinal direction is the direction of the reflecting tape 16. As a result of this arrangement, since the angle of the peak A or B of the optical sensor signal Y in FIG. 2 always indicates the upstream side of the longitudinal direction, the angle of such peak can be used as the reference angle. Further, since the distance from the peak A to the next peak B represents one revolution of the sheet, it is 360°. Therefore, since the direction of molecular orientation is associated with the angle at which the amount of deviation of the resonance frequency curve X is at a maximum, as described above, C and D in FIG. 2 correspond thereto and the angle from the reference can be found by computation.

Figure 3:
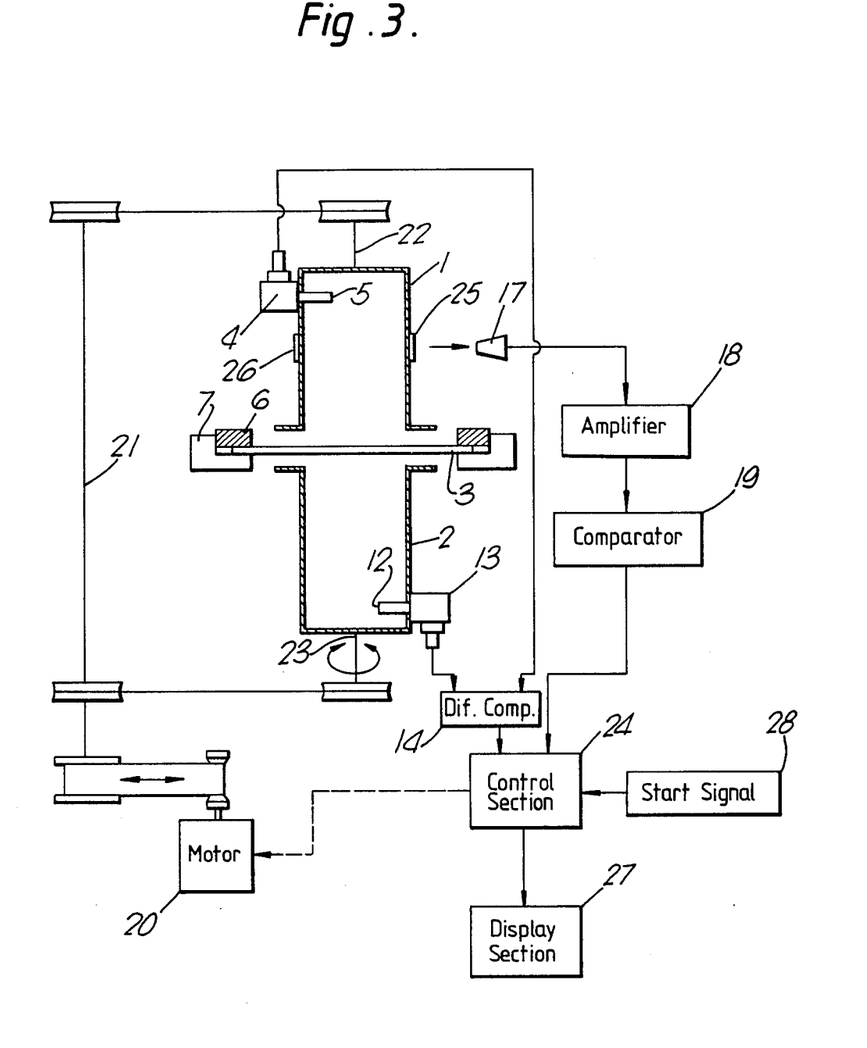

An embodiment shown in FIG. 3 is the same as that shown in FIG. 1 in that the sheet 3 is fixed on the sheet fixing block 7 by the keep ring plate 6 and is held between the upper and lower waveguides 1 and 2, but differs in that the waveguides 1 and 2 can be rotated while the sheet 3 is kept without being rotated. The synchronous rotation of the upper and lower waveguides 1 and 2 is achieved, as shown in FIG. 3, by connecting a reversible motor 20 for the waveguides, a drive shaft 21, and waveguide main shafts 22 and 23 by means of belts. In addition, it is desirable that the angle of rotation for the waveguides be set at a value greater than the angle of 180° needed for measurement, and the initial waiting angle and the next waiting angle can be defined by installing optical sensors, limit switches or the like for detecting the angles, at suitable positions.

While FIG. 3 shows the method of rotating the waveguides by using pulleys and belts, depending upon the objective there may be employed a method of directly rotating the plane of linear polarization as by connecting separate electric motors directly to the ends of the waveguides or applying a magnetic field to the upper waveguide.

The linearly polarized microwaves passing through the sheet 3 in the cavity resonator system, after passing through the lower waveguide 2, are received by the receiving antenna 12 and then converted into electric signals. Such electric signals are demodulated by a detector 13 and transferred to a control section 24.

To provide a rotative angle reference for this received output, for example, as shown in FIG. 3, narrow reflecting tapes 25 and 26 are applied, 180° apart, to two places on the lateral surface of the upper waveguide 1 so that variations in reflectance of monitor light are detected during rotation by an optical sensor 17 and the resulting electric signals are transferred via an amplifier 18 and a comparator 19 to a control section 24. In addition, since the transverse or longitudinal direction of the sheet is known in advance, the sheet 3, when attached to the sheet fixing block 7, is positioned so that for example the upstream side of the longitudinal direction is the direction of the reflecting tape 25. As a result of this arrangement, when the signal from the reflecting tape 25 is transferred from the optical sensor 17, it always indicates the upstream side of the longitudinal direction, so that such angle can be used as the reference angle.

Measurement is started when a measurement start signal enters the control section 24. The control section 24, on the basis of a program inputted thereinto in advance, emits a forward rotation start signal to the reversible motor 20, so that the two waveguides 1 and 2 start rotating in the forward direction from the initial wating angle. The control section 24 soon receives from the optical sensor 17 a signal indicating that the reflecting tape 25 has passed by, and it stores this signal as the measurement start angle and thereafter it also receives a signal notifying the passage of the reflecting tape 26 and stores this signal as the measurement termination angle and emits an operating stop signal to the reversible motor 20, stopping the waveguides 1 and 2 at the next waiting angle. The control section 24 computes the received resonance frequency values corresponding to the individual angles of rotation inputted thereinto from the detector 13 during the interval from measurement start angle to measurement stop angle, and according to the need it delivers its output to a display section 27 such as a CRT or an X-Y plotter.

Next, the sample on the sheet fixing block 7 is exchanged and a measurement start signal 28 is inputted again. The control section 24 this time gives a reverse rotation command to the reversible motor 20, causing the waveguides 1 and 2 to follow the course which is reverse to the previous one, so that the waveguides 1 and 2 are brought back to the initial waiting angle. Thereafter, the aforesaid procedure is repeated a predetermined number of times. In addition, the same computing operation is performed and the result is outputted to the display section 27.

Figure 4:
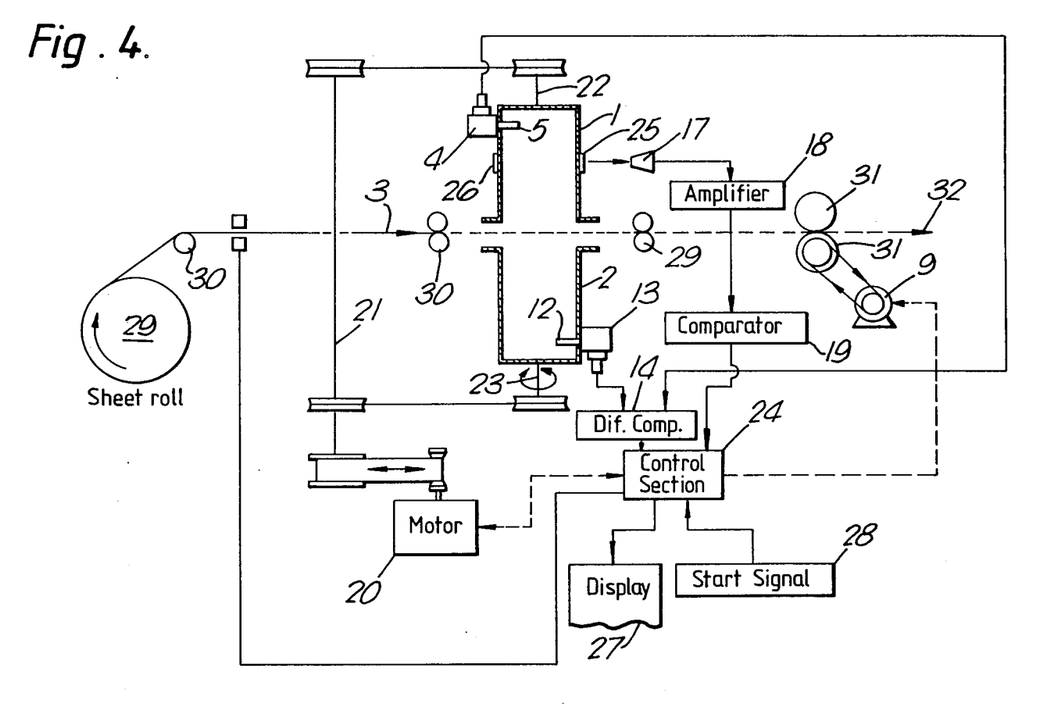

FIG. 4 shows an embodiment of the invention wherein to observe two-dimensional molecular orientation characteristics of of sheets, a narrow sample is taken in the flow direction or width direction from the sheet roll wound up at the reel part and the apparatus of the invention is applied to such sample. In addition, the polarization plane rotating mechanism and the detecting means using an optical sensor are the same as those shown in FIG. 3. A sheet roll 29 of narrow sample is unwound from an unillustrated reel stand and passed over a guide roll 30 and through the nip of sheet feed rolls 31. In addition, it is preferable to make it possible to take measurements from the front end of the sheet 3 by providing a lead tape 32 at said front end. Such sheet feed nip rolls 31 are driven by a variable speed motor 9. Further, its operation and stoppage are optionally set by signals from the control section 24.

To describe the usage in more detail, the operative speed of the reversible motor 20 is set to rotate the waveguides 1 and 2 at a required rotative speed, while the amount of rotation and measurement-intended stop time of the sheet feed motor 9 are set to feed the sheet 3 at a required speed. Further, the reflecting tape 25 for the waveguide 1 is set at the initial waiting angle, while the transmitting antenna 5 is emitting linearly polarized waves. When a measurement start signal 28 is sent to the control section 24, the latter emits an operation start signal to the sheet feed motor 9 on the basis of the program inputted thereinto in advance, and when the first measuring place reaches the middle between the waveguides 1 and 2, the control section emits an operation stop signal to the sheet feed motor 9 and at the same time it emits a forward rotation start signal to the reversible motor 20, which thereby rotates the waveguides 1 and 2 in the forward direction from the initial waiting angle. When the optical sensor 17 passes by the reflecting tape 26, a forward rotation stop signal is emitted to the reversible motor 20, and the waveguides are stopped at the next waiting angle. During this time, the control section 24 stores or memorizes as the first-time measured values the resonance frequencies corresponding to the individual angles 180° from the resonance frequencies received by the receiving antenna 12.

Subsequently, upon the lapse of the preset time, the control section 24 again operates the sheet feed motor 9 to feed the sheet 3 until its second-time measurement place stops and at the middle between the waveguides 1 and 2, while emitting a backward rotation start signal to the reversible motor 20. This time, reversely to the previous time, the waveguides 1 and 2 are reversely rotated from the waiting angle and the resonance frequencies corresponding to the individual angles in 180° are stored as the second-time measured measured values. Thereafter, the same procedure as the above are repeated and the results are computed and outputted to a display section 27 such as a printer, an X-Y plotter or the like. As for cavity resonators applicable to the present invention, those whose Q values as measured with a sheet put in are not less than at least several hundreds are preferable, since the higher the Q value, the greater the frequency deviation and the more distinct is anisotropy reflected.

Examples of the invention will now be described in detail, but it should be noted that the invention is not limited to such examples.

EXAMPLE 1

Figure 5:
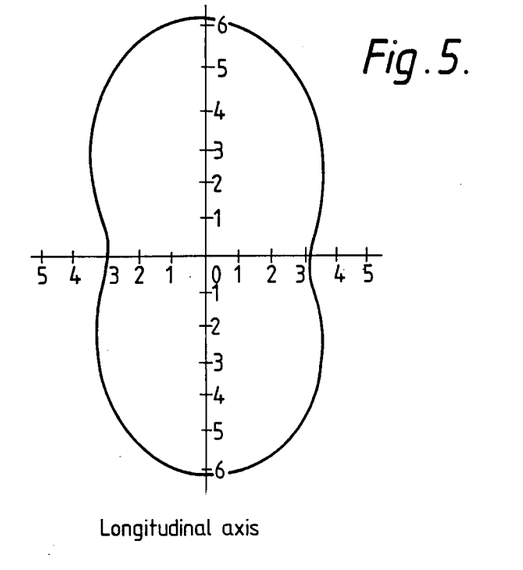
FIG. 5 shows an orientation graph obtained by the method of the invention applied to wood-free paper.

A sample of wood free paper having a reel air-dry weight of 45 g/m$^2$ and a reel moisture content of 7% from a Fourdrinier machine operating at a running speed of 450 m/min was measured by a molecular orientation or dielectric characteristic measuring apparatus of the arrangement shown in FIG. 1 used in the method of the invention. First, the upstream side of longitudinal direction of said sample was made the direction of the reflecting tape 16 and then while rotating the waveguides 1 and 2 1.0 rpm the sample was measured using linearly polarized sawtooth waves of 3.4–3.5 GHz (5 Hz sweep), whereby a graph was obtained as shown in FIG. 5 wherein the amounts of deviation corresponding to the individual angles are indicated by distances from the origin. As is clear from FIG. 5, since the direction in which the deviation is at a maximum coincides with the upward or downward direction, it was readily ascertained that in the sample in this example the fiber orientation was in the longitudinal direction.

Figure 6:
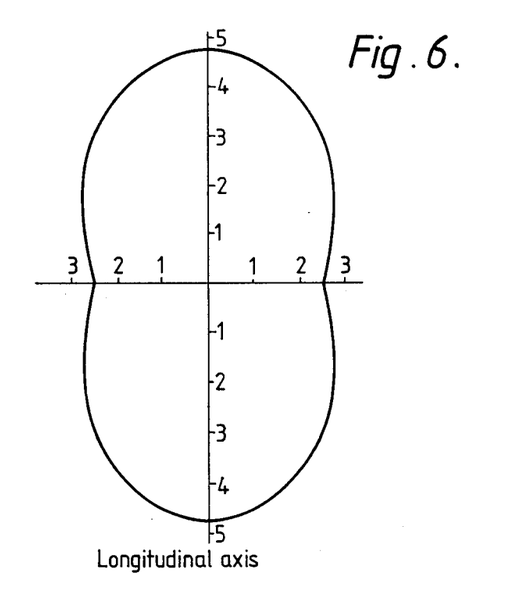
FIG. 6 shows a result obtained by the conventional zero-span tensile strength method using the same sample.

For comparing the aforesaid result with the conventional technique, the present method was compared with the method based on zero-span tensile strength measurement. The result obtained by the conventional zero-span tensile strength method is shown in FIG. 6. As is clear from a comparison between the two graphs, the direction in which the deviation was at a maximum significantly corresponded to the direction in which the tensile strength was at a maximum. However, the time needed from the time the sample was obtained until the completion of the determination of orientation was about 2 minutes in the present invention, whereas in the zero-span tensile strength method it was about 180 minutes or more.

EXAMPLE 2

Figure 7:
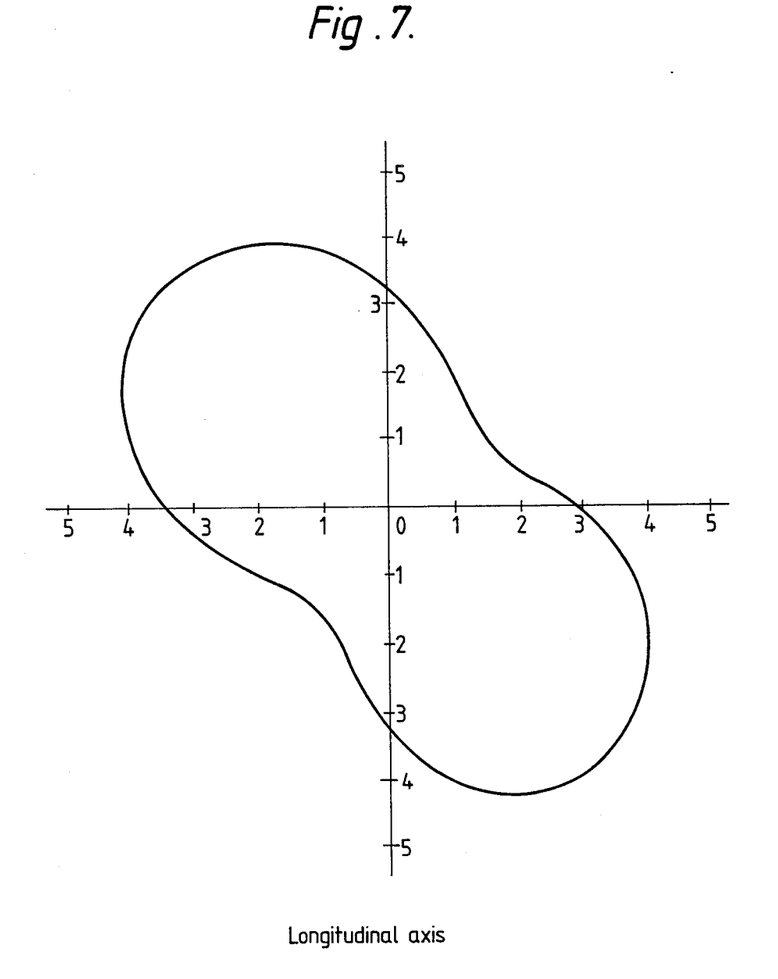
FIG. 7 shows an orientation graph obtained by the invention applied to polyethylene terephthalate.

A 70-μm thick polyethylene terephthalate sample obtained by stretching with a tenter-method biaxial stretching apparatus was measured by a molecular orientation or dielectric characteristic measuring apparatus constructed in the manner shown in FIG. 1 used in the present invention. The waveguides 1 and 2 used were in the form of a rectangle with an opening size of 58.1 mm×29.1 mm. First, the upstream side of longitudinal direction of said sample was made the direction of the reflecting tape 16 and then the sample was measured using linearly polarized sawtooth waves of 4.9–5.0 GHz (5 Hz sweep) while rotating it at 1.0 rpm. A graph was obtained as shown in FIG. 7 wherein the amounts of deviation corresponding to the individual angles are indicated by distances from the origin. As is clear from FIG. 7, since the direction in which the deviation is at a maximum coincides with the direction rotated through about 45° in the reverse direction from the longitudinal direction, it was readily ascertained that the direction of molecular orientation was the direction rotated counterclockwise through about 45° from the longitudinal direction. The time needed from the time the sample was obtained until the completion of determination of orientation was only about 5 minutes.

EXAMPLE 3

Figure 8:
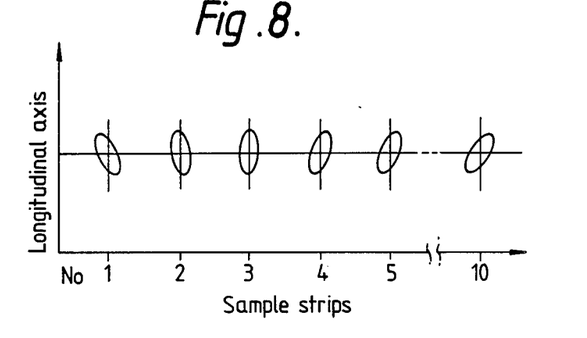
FIG. 8 shows an X-Y recorder output indicating the widthwise molecular orientation of said polyethylene terephthalate.

A 5-m wide polyethylene terephthalate sheet obtained under the same conditions as in Example 2 was slitted along the direction of flow into 10 equal strips to provide narrow samples. Such samples were measured by a molecular orientation dielectric characteristic measuring apparatus constructed in the same manner as shown in FIG. 4. A feed rate of 200 mm/pitch, a stop time of 1 second, and a rotative speed of the reversible motor 20 to provide a waveguide rotative speed of 1.0 rpm were set in the control section 24. The amounts of deviation corresponding to the individual angles of the narrow samples were obtained by optionally selecting 10 deviation values for the same angle measured in the direction of flow and averaging them; the chart indicating the output from X-Y recorder was shown in FIG. 8.

EXAMPLE 4

Figure 9:
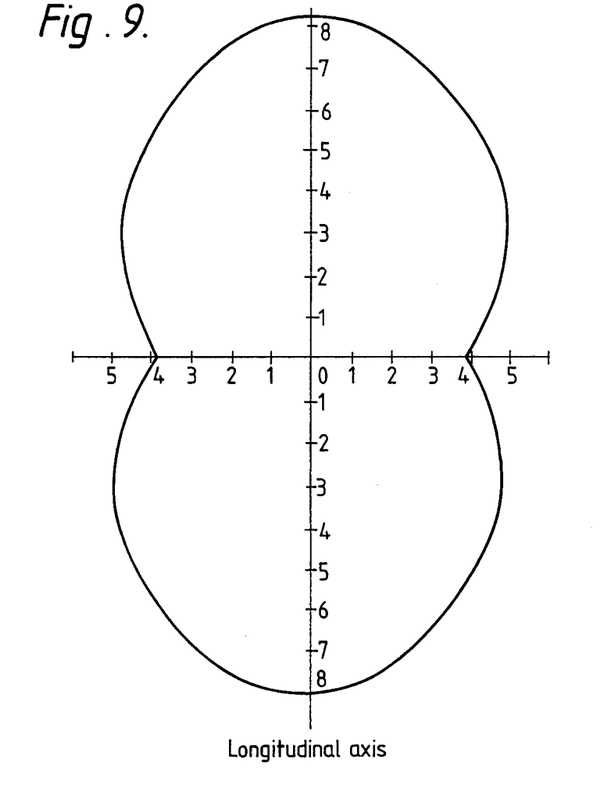
FIG. 9 shows a result obtained by applying the invention to an alumina silicate sheet which is a ceramic sheet.

A 100-μm thick alumina silicate sample obtained by the tape casting forming method was measured by the apparatus of the invention constructed in the manner shown in FIG. 3. Waveguides 1 and 2 having the same size and shape as those used in Example 1 were used, and the upstream side of longitudinal direction of said sample was made the direction of the reflecting tape 25 and then the sample was measured using linearly polarized sawtooth waves of 3.4–3.5 GHz (5 Hz sweep) while rotating the waveguides 1 and 2 at a rotative speed of 1.0 rpm. As a result, a graph as shown in FIG. 9 was obtained in which the amounts of deviation corresponding to the individual angles are indicated by distances from the origin. As is clear from FIG. 9, since the direction in which the deviation is at a maximum coincides with the upward or downward direction, in the sample in this example it was readily ascertained that the molecular orientation is in the longitudinal direction.

EXAMPLE 5

Figure 10:
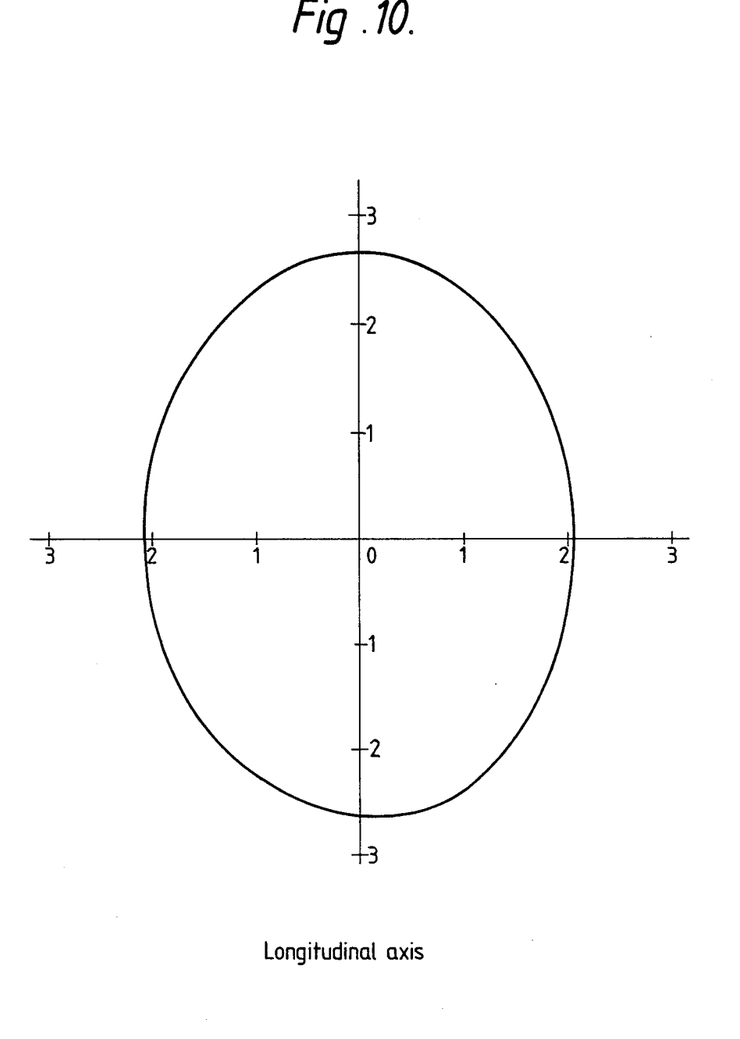
FIGS. 10 and 11 show a dielectric constant distribution and a dielectric loss factor distribution which are obtained by applying the invention as a polyoxymethylene sheet.
Figure 11:
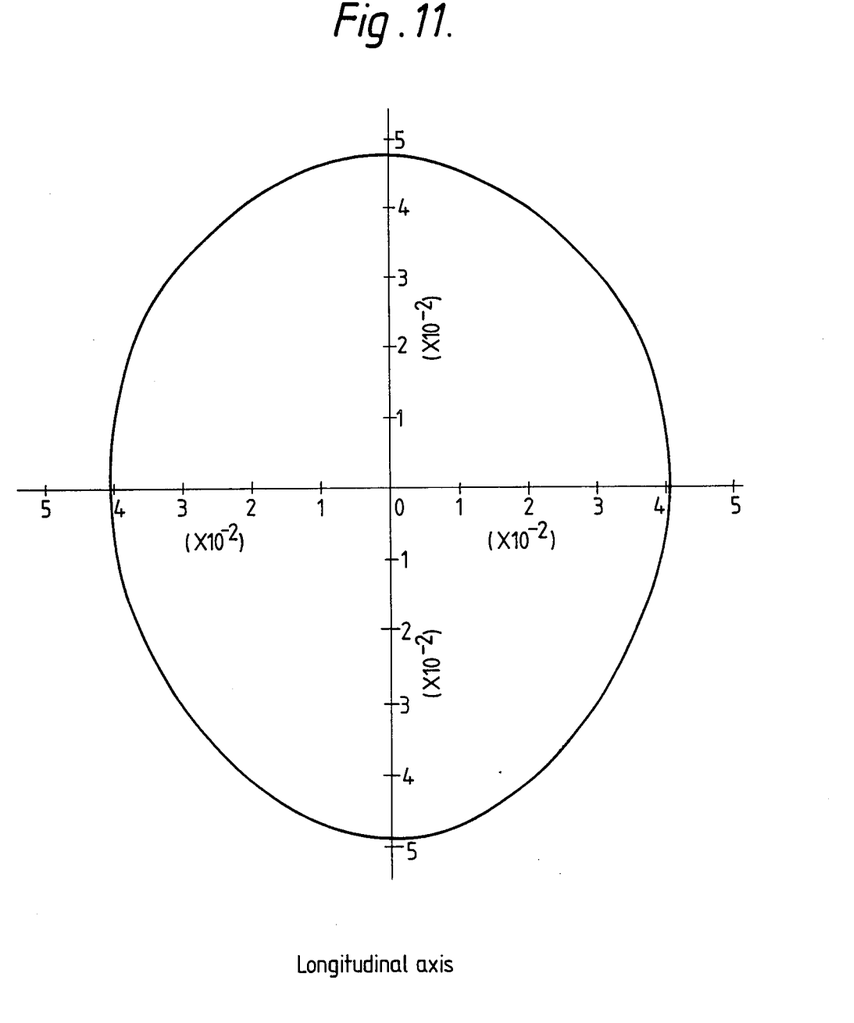

A 50-μm thick polyoxymethylene sample obtained by stretching to twice the longth with a uniaxial stretching apparatus was measured with waveguides having the same shape as in Example 2 using linearly polarized sawtooth waves of 3.43–3.48 GHz (5 Hz sweep) while rotating the sample intermittently in steps of 15° by a stepping motor. Graphs were obtained as shown in FIGS. 10 and 11 wherein dielectric constants and dielectric loss factors corresponding to the individual angles are indicated by distances from the origin. As is clear from FIGS. 10 and 11, in the case of polyoxymethylene, degrees of dependency of $\epsilon_2$ and $\epsilon_2'$ on angle are approximately equal. Further, the time needed for measurement after the sample was obtained was 3 minutes.

According to the molecular orientation or dielectric characteristic measuring apparatus of the invention, a checkup of the molecular orientation or dielectric characteristic of sheets can be made extremely easily and in a short time, making it possible to cope with abnormality during its early stage, so that the occurrence of rejects can be kept to a minimum.

What is claimed is:

1. A method of measuring the molecular orientation of the constituents of a dielectric sheet or web by means of dielectric constant and/or dielectric loss, comprising the steps of inserting a sample portion of the dielectric sheet or web in a small clearance in a cavity resonator formed by a pair of waveguides, each of said waveguides having a rectangular cross section which is open at one end thereof, one of said waveguides having a transmitting antenna and the other waveguide having a receiving antenna, said waveguides being spaced apart from each other with their openings defining said clearance therebetween, irradiating said sample portion with frequency sweep type linearly polarized microwaves emitted by said transmitting antenna and its associated waveguide perpendicularly to said sample portion, producing a relative rotation between the plane of polarization of said microwaves and said sample portion around the axis of said cavity resonator by rotating said dielectric sheet or web relative to said pair of waveguides, measuring the resonance frequency "f" of the microwaves received by said receiving antenna and/or Q value "Q" of the waveguides with the sample portion located at predetermined angular positions so as to interrupt the relative rotation for each aforesaid measurement, and thereafter determining anisotropic dielectric constants and/or anisotropic dielectric losses from the relation between the resonance frequencies "f" and "fo" and/or the relation between the value "Q" and "Qo", wherein the "fo" and "Qo" are the resonance frequency and the Q value in the initial state of the waveguides without the sample portion.

2. A method as set forth in claim 1, wherein the orientation of the constituent of one sample portion is measured during 180° rotation of said cavity resonator, whereupon the web or sheet including this sample portion is advanced one step to insert the subsequent sample portion into said small clearance and the orientation of the constituent of this portion is measured, such operation being repeated.

* * * * *